(12) United States Patent
Wietzorrek (10) Patent No.: US 10,564,102 B2
(45) Date of Patent: Feb. 18, 2020

(54) OPTICS FOR ANALYSIS OF MICROWELLS

(71) Applicant: Roche Molecular Systems, Inc., Pleasanton, CA (US)

(72) Inventor: Joachim Wietzorrek, Zug (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 414 days.

(21) Appl. No.: 15/437,854

(22) Filed: Feb. 21, 2017

(65) Prior Publication Data

US 2017/0241912 A1     Aug. 24, 2017

(30) Foreign Application Priority Data

Feb. 22, 2016 (EP) .................................... 16156735

(51) Int. Cl.
*G01N 21/64* (2006.01)
*G02B 17/06* (2006.01)
(Continued)

(52) U.S. Cl.
CPC ......... *G01N 21/6456* (2013.01); *C12Q 1/686* (2013.01); *G01N 21/6452* (2013.01); *G02B 17/008* (2013.01); *G02B 17/0605* (2013.01); *G02B 17/0812* (2013.01); *H04N 5/2256* (2013.01); *G01N 21/253* (2013.01); *G01N 2021/6463* (2013.01); *G01N 2035/0418* (2013.01); *G01N 2201/0245* (2013.01); *G01N 2201/0631* (2013.01); *G02B 27/0025* (2013.01)

(58) Field of Classification Search
CPC ........... G01N 21/6456; G01N 21/6452; G01N 2035/0418; C12Q 1/686; G02B 17/0605; G02B 27/0025; G02B 27/008; G02B 21/16
See application file for complete search history.

(56) References Cited

U.S. PATENT DOCUMENTS 4,068,947 A    1/1978 Buckley et al.
7,545,446 B2   6/2009 Lerner et al.
(Continued)

FOREIGN PATENT DOCUMENTS

EP    1681556 A1    7/2006
EP    2075615 A1    1/2009
(Continued)

OTHER PUBLICATIONS

European Search Report 16156735.9, dated Aug. 2, 2016.

*Primary Examiner* — Maurice C Smith
(74) *Attorney, Agent, or Firm* — Pamela C. Ancona (57) ABSTRACT

In one aspect of the present disclosure an optical measurement device includes a sample holder defining a sample plane, wherein the sample holder is configured to arrange a sample carrier including an array of measurement positions in the sample plane, an illumination unit configured to illuminate the sample plane, a detector and an optical imaging system configured to image the sample plane including the array of measurement positions onto the detector, the optical imaging system including two or more curved reflective elements adapted to image the sample plane onto the detector with a magnification of between 2:1 and 1:2 and the detector being configured to take an image of all measurement positions of the array of measurement positions at a time.

14 Claims, 5 Drawing Sheets

(51) Int. Cl.
*G02B 17/00* (2006.01)
*C12Q 1/686* (2018.01)
*G02B 17/08* (2006.01)
*H04N 5/225* (2006.01)
G01N 21/25 (2006.01)
G01N 35/04 (2006.01)
G02B 27/00 (2006.01)

(56) References Cited

U.S. PATENT DOCUMENTS

| | | |
|---|---|---|
| 8,599,383 B2 | 12/2013 | Teitell et al. |
| 2004/0233545 A1 | 11/2004 | Jiang et al. |
| 2009/0112482 A1* | 4/2009 | Sandstrom ......... G01N 21/6452 702/19 |
| 2010/0038559 A1 | 2/2010 | Feke et al. |
| 2015/0204784 A1 | 7/2015 | Crandall et al. |
| 2015/0370058 A1* | 12/2015 | Bouzid ................ G06F 16/284 359/366 |
| 2016/0055632 A1* | 2/2016 | Fu ....................... G01N 21/274 382/129 |

FOREIGN PATENT DOCUMENTS

| | | |
|---|---|---|
| EP | 2713154 A1 | 4/2014 |
| EP | 2960644 A1 | 12/2015 |
| WO | 2002014838 A2 | 2/2002 |

\* cited by examiner

OPTICS FOR ANALYSIS OF MICROWELLS

CROSS-REFERENCE TO RELATED APPLICATIONS

The present application claims the benefit of priority under 35 U.S.C. § 119 of EP16156735.9, filed Feb. 22, 2016, the content of which is incorporated herein by reference in its entirety.

TECHNICAL FIELD

This disclosure relates to imaging optical measurement devices and optical imaging methods. In particular, this disclosure relates to imaging optical measurement devices and methods for biological samples.

BACKGROUND

In today's laboratory environments optical measurements play an important role. For example, fluorescence measurements can be used to qualitatively or quantitatively analyze a biological sample. In the course of this process, fluorescent light re-emitted from a particular target contained in the biological sample is collected and the sample can be characterized based on the detected fluorescent light. Sample volumes used in these processes can be fairly small. For instance, in analyzers for characterizing samples containing nucleotides multiplied by polymerase chain reaction (PCR), sample volumes of only a few microliters or less are not uncommon. As a consequence, a number of fluorescent molecules or entities contained in a particular sample can be fairly low. This, in turn, can result in fairly low fluorescent light intensities of the re-emitted light and correspondingly low signal intensities of optical measurement devices in PCR analyzers.

In this situation, one strategy can be to increase the integration time of the optical sampling process to account for the low signal intensities. However, analyzer time is a valuable good so that simply extending the integration time of the measurement system might not be a viable or desirable option in many situations. Moreover, simply increasing the sampling time might also cause other issues, e.g., due to noise or sample degradation.

SUMMARY

In a first general aspect an optical measurement device includes a sample holder defining a sample plane, wherein the sample holder is configured to arrange a sample carrier including an array of measurement positions in the sample plane, an illumination unit configured to illuminate the sample plane, a detector and an optical imaging system configured to image the sample plane including the array of measurement positions onto the detector, the optical imaging system including two or more reflective elements adapted to image the sample plane onto the detector with a magnification of between 2:1 and 1:2 and the detector being configured to take an image of all measurement positions of the array of measurement positions at a time.

In a second general aspect of the present disclosure an optical measurement device for biological samples is described. The optical measurement device for fluorescence detection comprises a sample holder defining a sample plane, the sample holder being configured to arrange a sample carrier including an array of measurement positions in the sample plane, an illumination unit configured to illuminate the sample plane in a trans-illumination setup, a detector and an optical imaging system configured to image the sample plane including the two dimensional array of measurement positions onto the detector, the optical imaging system including two or more reflecting imaging elements adapted to image the sample plane onto the detector and an output numerical aperture of the illumination system being larger than an input numerical aperture of the imaging system.

In a third general aspect of the present disclosure a method for imaging a sample carrier having an array of measurement positions containing samples includes illuminating the array of measurement positions, collecting light emitted from all measurement positions of the array of measurement positions at a time and imaging the collected light onto a detector by using two or more curved reflective elements adapted to image the sample plane onto the detector with a magnification of between 2:1 and 1:2.

Therefore, the disclosure provides an optical measurement device, comprising:

a sample holder defining a sample plane, wherein the sample holder is configured to arrange a sample carrier including an array of measurement positions in the sample plane;

an illumination unit configured to illuminate the sample plane;

a detector;

an optical imaging system configured to image the sample plane including the array of measurement positions onto the detector, wherein the optical imaging system includes two or more curved reflective elements adapted to image the sample plane onto the detector with a magnification of between 2:1 and 1:2, and wherein the detector is configured to take an image of all measurement positions of the array of measurement positions at a time.

In this embodiment, the two or more curved reflective elements include two or more curved mirror elements. Specifically, the two or more curved reflective elements include exactly two curved mirror elements. Two of the two or more curved reflective elements can have a common center of curvature. Moreover, the two or more reflective elements are arranged in an Offner-type configuration (see, e.g., U.S. Pat. No. 7,545,446, the disclosure of which is incorporated herein by reference).

The magnification of the optical imaging system can be between 1.2:1 and 1:1.2, e.g., the magnification is substantially 1.

The illumination unit can be an epi-illumination unit. Moreover, the illumination unit can be configured to illuminate the sample plane under critical lighting conditions. Still further, the illumination unit can further include a homogenizer adapted to increase the homogeneity of the illumination in the sample plane. The homogenizer can include a light guide, e.g., a rod-shaped light guide. In this example, the illumination unit can include a primary light source that generates light that is homogenized by the homogenizer, wherein light output by the homogenizer acts as a secondary light source whose output is imaged onto the sample plane. The secondary light can illuminate a tilted field stop, and optionally, the output of the secondary light is imaged onto the sample plane by a relay lens.

In a specific embodiment, the illumination unit can be arranged to reduce a keystone distortion. The keystone effect is caused when one attempts to project an image onto a surface at an angle, as with a projector that is not centered onto the screen on which it is projecting. It is a distortion of the image dimensions, e.g., making a square look like a trapezoid, the shape of an architectural keystone, hence the name of the feature. In the typical case of a projector sitting on a table, and looking upwards to the screen, the image is larger at the top than on the bottom. Some areas of the screen may not be focused correctly as the projector lens is focused at the average distance only. In photography, the term is used to describe the apparent leaning of buildings towards the vertical centerline of the photo when shooting upwards, a common effect in architectural photography. Likewise, when taking photos looking down, e.g., from a skyscraper, buildings appear to get broader towards the top. The effect is usually corrected for by either using special lenses in Tilt-shift photography or in post-processing using modern image editing software.

Moreover, the illumination unit can be arranged as a Scheimpflug-type illuminator. The Scheimpflug principle is a geometric rule that describes the orientation of the plane of focus of an optical system (such as a camera) when the lens plane is not parallel to the image plane. It is commonly applied to the use of camera movements on a view camera. Normally, the lens and image (film or sensor) planes of a camera are parallel, and the plane of focus is parallel to the lens and image planes. If a planar subject (such as the side of a building) is also parallel to the image plane, it can coincide with the plane of focus, and the entire subject can be rendered sharply. If the subject plane is not parallel to the image plane, it will be in focus only along a line where it intersects the plane of focus. When an oblique tangent is extended from the image plane, and another is extended from the lens plane, they meet at a line through which the plane of focus also passes. With this adjustment, a planar subject that is not parallel to the image plane can be completely in focus. (See, e.g., http://www.trenholm.org/hmmerk/#SR, the disclosure of which is incorporated herein by reference.) An example of a Scheimpflug Illuminator or Imaging System is the Scheimpflug Pentacam System (Oculus, Arlington, Wash.; http://www.oculus.de/us/products/pentacam/pentacam-pentacam-hr-pentacam-axl/, the disclosure of which is incorporated herein by reference).

Still further, the illumination unit can include a baffle to blank out rays of illumination light propagating under a predetermined range of angles in relation to a main optical axis of the illumination unit. The baffle can be arranged to blank out rays propagating at angles below a threshold angle in relation to a main optical axis of the illumination unit.

In a further embodiment, the illumination unit can be a trans-illumination unit.

The illumination unit can be configured so that an output numerical aperture of the illumination unit is greater than a numerical aperture of the imaging system.

In a specific embodiment, the illumination unit includes one or more light emitting diodes.

Moreover, the optical measurement device described herein can include a path of at least a portion of the light rays generated by the illumination unit at least partially overlapping with a path of a portion of the rays imaged onto the detector by the optical imaging system.

The device can also include one or more plane minors to fold the optical path of the imaging system, the illumination system, or both. In addition, a dichroic mirror can be included that is arranged to couple in light generated by the illumination unit. In a specific embodiment, the dichroic mirror can be arranged to deflect light emitted by a sample contained in the sample carrier and imaged by the imaging system onto the detector.

In a specific embodiment, the illumination unit and the imaging system do not share optical elements. In one embodiment, an optical path of rays of illumination light generated by the illumination unit is completely separate from an optical path of light imaged by the imaging system. For example, an optical path of rays of illumination light generated by the illumination unit at least partially overlaps with an optical path of light imaged by the imaging system. The field of view of the optical imaging system can substantially match the size of a detection area of the light detecting device.

The sample carrier contemplated in the description below can be a microwell plate. The sample carrier can include an array of wells for receiving fluid samples, each well defining a measurement position. In a particular embodiment, the spacing of the array is below 2 mm, e.g., below 1 mm, more specifically below 250 μm. The area of a measurement position can correspond to a surface area of a microwell plate.

The light detecting device can include a plurality of pixels having a pixel size which is smaller than an area of a measurement position. In a specific embodiment, the size of a pixel in the light detecting device can be smaller than 20 μm, e.g., smaller than 10 μm.

The imaging system described herein can include a correction element adapted to at least partially correct aberrations induced by a dichroic mirror, e.g., aberrations including but not limited to an astigmatic aberration. The device can include a dichroic mirror positioned in the optical path of the imaging system and the correction element is tilted about an axis which is orthogonal to a tilt axis of the dichroic mirror. The optical path can include an optical filter to block illumination light from being imaged onto the detector.

The optical measurement device described herein can be configured to image fluorescent light generated by a sample contained in the sample carrier.

The sample holder can be stationary relative to the imaging system during imaging of the array of measurement positions in the sample plane.

In a specific embodiment, the optical measurement device is part of a PCR system.

The disclosure specifically contemplates an optical measurement device for fluorescence detection, comprising:

a sample holder defining a sample plane, wherein the sample holder is configured to arrange a sample carrier including an array of measurement positions in the sample plane;

an illumination unit configured to illuminate the sample plane in a trans-illumination setup;

a detector;

an optical imaging system configured to image the sample plane including the array of measurement positions onto the detector, wherein the optical imaging system includes two or more curved reflective elements adapted to image the sample plane onto the detector with a magnification of substantially 1, wherein an output numerical aperture of the illumination system is larger than an input numerical aperture of the imaging system; and wherein the detector is configured to take an image of all measurement positions of the array of measurement positions at a time.

Also contemplated is an optical measurement device for fluorescence detection, comprising:

a sample holder defining a sample plane, wherein the sample holder is configured to arrange a sample carrier including an array of measurement positions in the sample plane;

an illumination unit configured to illuminate the sample plane in a trans-illumination setup;

a detector;

an optical imaging system configured to image the sample plane including the two dimensional array of measurement positions onto the detector, wherein the optical imaging system includes two or more reflecting imaging elements adapted to image the sample plane onto the detector, and wherein an output numerical aperture of the illumination system is larger than an input numerical aperture of the imaging system.

Still further, the disclosure provides a method for imaging a sample carrier having an array of measurement positions containing samples, the method comprising:

illuminating the array of measurement positions;

collecting light emitted from all measurement positions of the array of measurement positions at a time;

imaging the collected light onto a detector by using two or more curved reflective elements adapted to image the sample plane onto the detector with a magnification of between 2:1 and 1:2.

In this embodiment, the magnification can be between 1.2:1 and 1:1.2, e.g., substantially 1. Moreover, the sample carrier can be a well plate, e.g., a microwell plate, and each measurement position corresponds to a well of the well plate.

The methods described herein also include using a light detector that includes a plurality of pixels having a size which is smaller than a measurement area of a measurement position. The measurement area of a measurement position can correspond to a surface area of a well of a microwell plate.

In a specific embodiment, the light emitted from all measurement positions is fluorescent light; the samples are biological samples, e.g., including nucleotides, e.g., PCR samples.

DETAILED DESCRIPTION

The devices and methods described herein provide a number of advantages. Firstly, the devices and methods of the present disclosure can allow for a faster detection of signals (e.g., fluorescent light) emitted from different measurement positions of a sample (e.g., different wells of a microwell plate) in some situations. For instance, some prior art analyzers scan different measurement positions sequentially. In contrast to that, the techniques of the present disclosure can facilitate imaging and capturing different measurement positions simultaneously (e.g., multiple or even all wells of a microwell plate) in some situations.

Secondly, by using the techniques of the present disclosure an optical measurement device can be constructed in a less complex fashion than some prior art optical measurement devices in some examples. As already mentioned, some prior art devices use a sequential approach to scan through different measurement positions (e.g., wells of a microwell plate). This can require actuators adapted to move the sample or the imaging optics or active optical components (e.g., a digital micro-mirror device) adapted to change an illumination pattern of the optical measurement device to sequentially address the different measurement positions. These arrangements can require a large number of moving parts or fairly expensive parts in some examples. The techniques of the present disclosure can at least partially render superfluous such elements by imaging multiple (e.g., all) measurement positions at the same time.

Thirdly, the imaging devices of the present disclosure can experience a relatively low level of optical aberrations as a result of the utilization of reflective elements and a relatively low magnification. At the same time, the comparatively low level of aberrations can be achieved in a relatively cost efficient manner. On the one hand, the imaging devices of the present disclosure can have a comparatively low chromatic aberration by using reflective elements. Therefore, the imaging devices of the present disclosure might not need compensation elements to compensate for chromatic aberrations in some examples that might be employed in some lens-based imaging systems (or can achieve the same level of compensation by employing less sophisticated compensators).

On the other hand, the relatively low magnification of the imaging devices of the present disclosure can reduce a level of aberrations in some examples. This can be of particular concern when analyzing small sample quantities contained in correspondingly small vessels. For example, a well diameter of a microwell plate can be lower than 50 µm and a distance between two wells of the microwell plate can be lower than 40 µm. While imaging structures of this size aberrations can be of particular concern as light from different measurement positions might not be clearly discernible as a result of the aberrations.

Some prior art optical measurement devices are equipped with imaging elements having a relatively high magnification (e.g., 20 times or larger). This can increase the level of optical aberrations and/or can make compensating the errors due to aberrations more difficult and/or costly. For instance, some lens-based systems with high-magnification employ microscope objectives with a plurality of lenses to compensate for aberrations that would occur when using only two lenses. This can make the imaging system more costly and error-prone. Thus, the imaging devices of the present disclosure might reduce the complexity, reliability and cost of the optical measurement device in some examples.

Fourthly, the techniques of the present invention can provide for a comparatively large field of view while at the same time providing a relatively large numerical aperture. In this manner, different measurement positions can be detected at the same time while collecting a comparatively high number of photons from each measurement position (and thus shortening a measurement duration). In some prior art systems (e.g., fluorescence microscopes) a field of view can be smaller than in the imaging devices of the present disclosure when similar numerical apertures shall be achieved (e.g., due to the fact that objectives with high numerical apertures tend to have a high magnification and thus small field of view).

In particular, the techniques of the present disclosure can achieve a high numerical aperture by using a trans-illumination unit to illuminate a sample which is separate from the imaging system. In this manner, a sample can be illuminated with a comparatively large output side numerical aperture without interfering with the imaging side of the system. As a result of the comparatively large illumination side numerical aperture, a comparatively large number of photons reach the sample and can be available to elicit a fluorescent response. In some prior art systems using an epi-illumination setup in which the illumination light at least partially passes through the same optical elements as the fluorescent light (e.g., through a microscope objective) it might not be feasible to work with a high illumination side numerical aperture. In these systems the output numerical aperture of the illumination unit cannot be (much) larger than the input side numerical aperture of the imaging system.

After having provided an overview over the techniques of the present disclosure, in the following paragraphs several terms will be discussed which are used in the present disclosure in a particular manner.

The term 'light' as used in the present disclosure includes but is not limited to radiation in the visible wavelength range. In some examples, light can include radiation having a wavelength of over 150 nm and below 10.000 nm (for instance, a wavelength between 350 nm and 1500 nm).

The term 'luminescent light' as used in the present disclosure includes fluorescent light (e.g., light generated as result of a singlet-singlet-transition) and phosphorescent light (e.g., light generated as result of a triplet-singlet-transition).

The term 'array of measurement positions' includes any spatial arrangement of two or more measurement positions. In one example, the array of measurement positions can include a rectangular array of N×M measurement positions (N and M being integer numbers larger than zero where at least one of M and N is an integer number larger than one). However, in other examples the array of measurement positions includes a non-rectangular array of measurement positions (e.g., a circular array of measurement positions). The array of measurement positions can arrange the measurement positions in a regular or irregular manner. In one example, an array of measurement positions includes an array of N×M (N and M being integer numbers larger than zero where at least one of M and N is an integer number larger than one) receptacles configured to contain biological samples. For instance, an array of measurement positions can include an array of N×M (N and M being integer numbers larger than zero where at least one of M and N is an integer number larger than one) wells of a microwell plate configured to contain biological samples.

The term 'optical measurement device for biological samples' can include any manual, semi-automated or automated measurement device configured to conduct optical measurements on biological samples. For instance, the 'optical measurement device for biological samples' of the present disclosure can be part of an analyzer or an analytical work cell for analyzing biological samples.

The terms 'analyzer,' 'analytical work cell,' and 'analytical unit' as used herein encompass any apparatus or apparatus component that can measure analytical properties of a biological sample, e.g. following a reaction of a biological sample with a reagent for obtaining a measurement value.

An analyzer is operable to a parameter value of the sample or a component thereof. Apart from the optical measurement devices of the present disclosure an analyzer can include measurement devices to determine a parameter value of the sample via one or more chemical, biological, physical, or other technical procedures.

An analyzer may be operable to measure said parameter of the sample or of at least one analyte and return the obtained measurement value. The list of possible analysis results returned by the analyzer comprises, without limitation, concentrations of the analyte in the sample, a qualitative (yes or no) result indicating the existence of the analyte in the sample (corresponding to a concentration above the detection level), optical parameters, DNA or RNA sequences, data obtained from mass spectrometry of proteins or metabolites and physical or chemical parameters of various types.

An analytical work cell may comprise units for pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow is optimized for certain types of analysis. Examples of such analyzers are clinical chemistry analyzers, coagulation chemistry analyzers, immunochemistry analyzers, urine analyzers, hematology analyzers, nucleic acid analyzers, used to detect the result of chemical or biological reactions or to monitor the progress of chemical or biological reactions.

The term 'biological sample' refers to material(s) that may potentially contain an analyte of interest. The biological sample can be derived from any biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The biological sample can be pretreated prior to use, such as preparing plasma from blood. Methods of treatment can involve centrifugation, filtration, distillation, dilution, concentration and/or separation of sample components including analytes of interest, inactivation of interfering components, and the addition of reagents. A biological sample may be used directly as obtained from the source or used following a pretreatment to modify the character of the sample. In some embodiments, an initially solid or semi-solid biological material can be rendered liquid by dissolving or suspending it with a suitable liquid medium. In some examples, the sample can be suspected to contain a certain antigen or nucleic acid.

In some examples, the biological sample can include nucleic acids amplified from an input biological sample containing nucleic acids by polymerase chain reaction.

The optical measurement devices and optical imaging methods of the present disclosure will subsequently be discussed in more detail.

First, in connection with FIG. 1 an example optical measurement device according to the present disclosure will be discussed. Subsequently, in connection with FIG. 2 to FIG. 4, variants of optical measurement devices according to the present disclosure will be explained in more detail. Last, in connection with FIG. 5 the integration of the optical measurement devices of the present disclosure in an analyzer for biological samples will be discussed.

Figure 1:
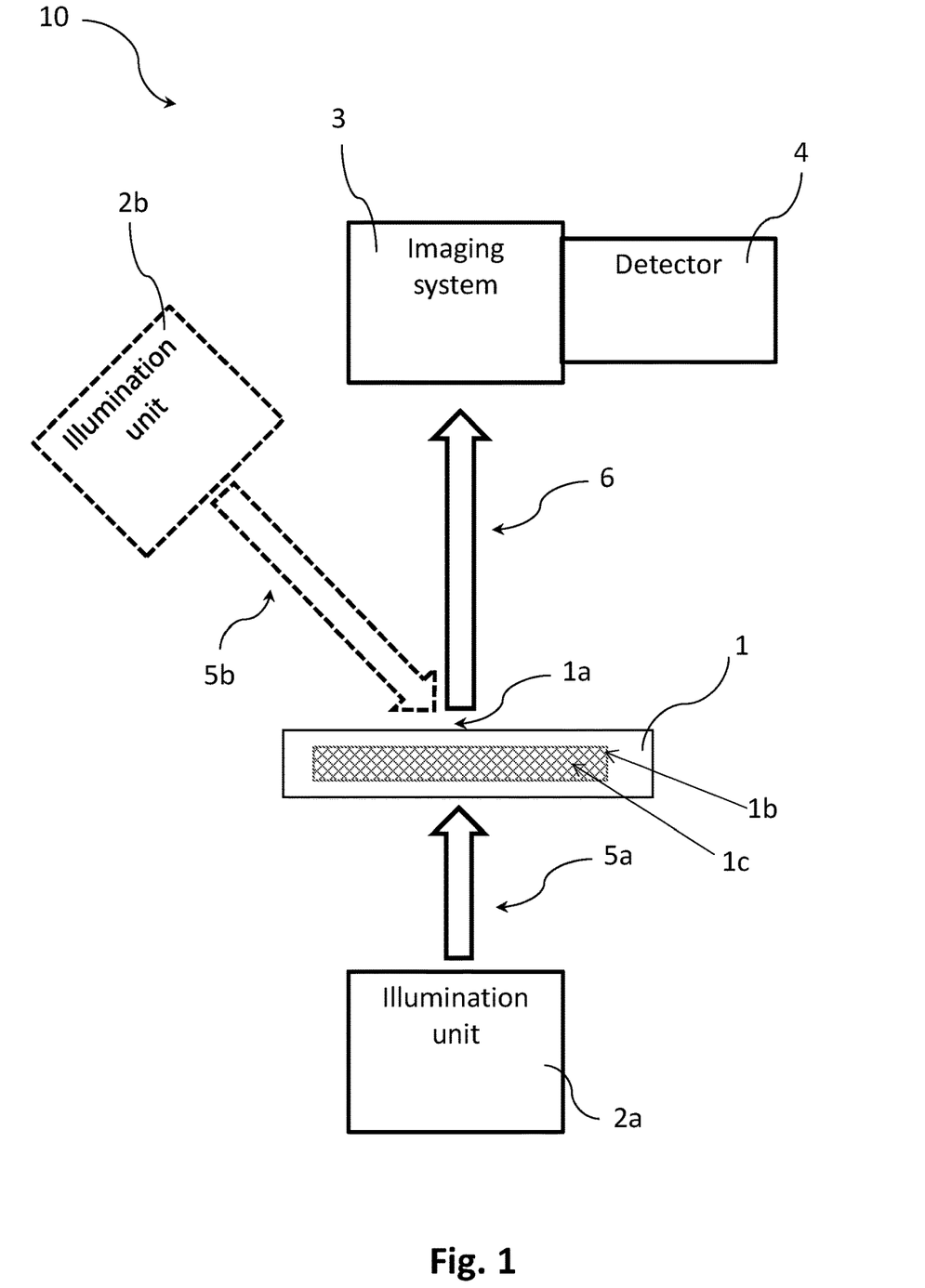
FIG. 1 shows a schematic drawing of an example optical measurement device according to the present disclosure.

FIG. 1 shows a schematic drawing of an example optical measurement device according to the present disclosure.

The optical measurement device includes a sample holder 1 defining a sample plane 1a, the sample holder being configured to arrange a sample carrier 1b including an array of measurement positions 1c in the sample plane, an illumination unit 2a, 2b configured to illuminate the sample plane, a detector 4 and an optical imaging system 3 configured to image the sample plane including the array of measurement positions onto the detector 4, the optical imaging system 3 including two or more curved reflective elements (not shown in FIG. 1) adapted to image the sample plane onto the detector 4 with a magnification of between 2:1 and 1:2 and the detector being configured to take an image of all measurement positions of the array of measurement positions at a time.

As can be seen in FIG. 1, the illumination unit can be an epi-illumination unit 2b (i.e., the illumination light 5b impinges on the same side of the sample from which collection light 6 is collected by an imaging system 3). In other examples, the illumination unit can be a trans-illumination unit 2a (i.e., the illumination light 5a impinges on the sample on the opposite side from which collection light 6 is collected by an imaging system 3). In still other examples, the optical measurement device can include a plurality of different illumination units (e.g., one or more trans-illumination units and one or more epi-illumination units).

The illumination light 5a, 5b interacts with the sample which re-emits collection light 6 which is imaged onto the detector 4 (i.e., the illumination light is photo-luminescent light emitted by the sample). In one example, the re-emitted collection light 6 is fluorescent light emitted by fluorophores of the sample (e.g., auto-fluorescence generated by constituents of a bodily substance or fluorescent light generated by fluorescent markers or probes attached to a target contained in the biological sample).

In the remaining description, the techniques of the present disclosure will be discussed in connection with examples in which fluorescent light is detected by the optical measurement device. However, the optical measurement devices of the present disclosure are not limited to detection of fluorescent light. In other examples, luminescent light in general can be detected (e.g., phosphorescent light).

In still other examples, the optical measurement devices of the present disclosure can be configured to detect scattered light. In still other examples, the optical measurement devices of the present disclosure can be configured to directly image a sample arranged in the sample holder 1. The optical measurement device for fluorescent measurements described herein can also be utilized for these applications (with appropriate modifications).

The sample carriers of the present disclosure can be any suitable receptacles configured to contain a biological sample. In one example, the sample carrier is a microwell plate including a plurality of wells. Each well can include a biological sample (e.g., between 0.1 µL and 100 µL of a biological sample). A diameter of a well of the microwell plate can be lower than 1 mm (e.g., lower than 500 µm or lower than 200 µm). In one example a diameter of a well of the microwell plate can range between 25 µm and 150 µm. In addition or alternatively, a spacing between two wells of the microwell plate can be lower than 0.7 mm (e.g., lower than 300 µm or lower than 100 µm). In one example, a spacing between two wells of the microwell plate can range between 20 µm and 50 µm.

After having given a short overview in connection with FIG. 1, different aspects of the optical measurement devices according to the present disclosure will be subsequently explained in more detail in connection with the examples of FIG. 2 to FIG. 4.

Figure 2:
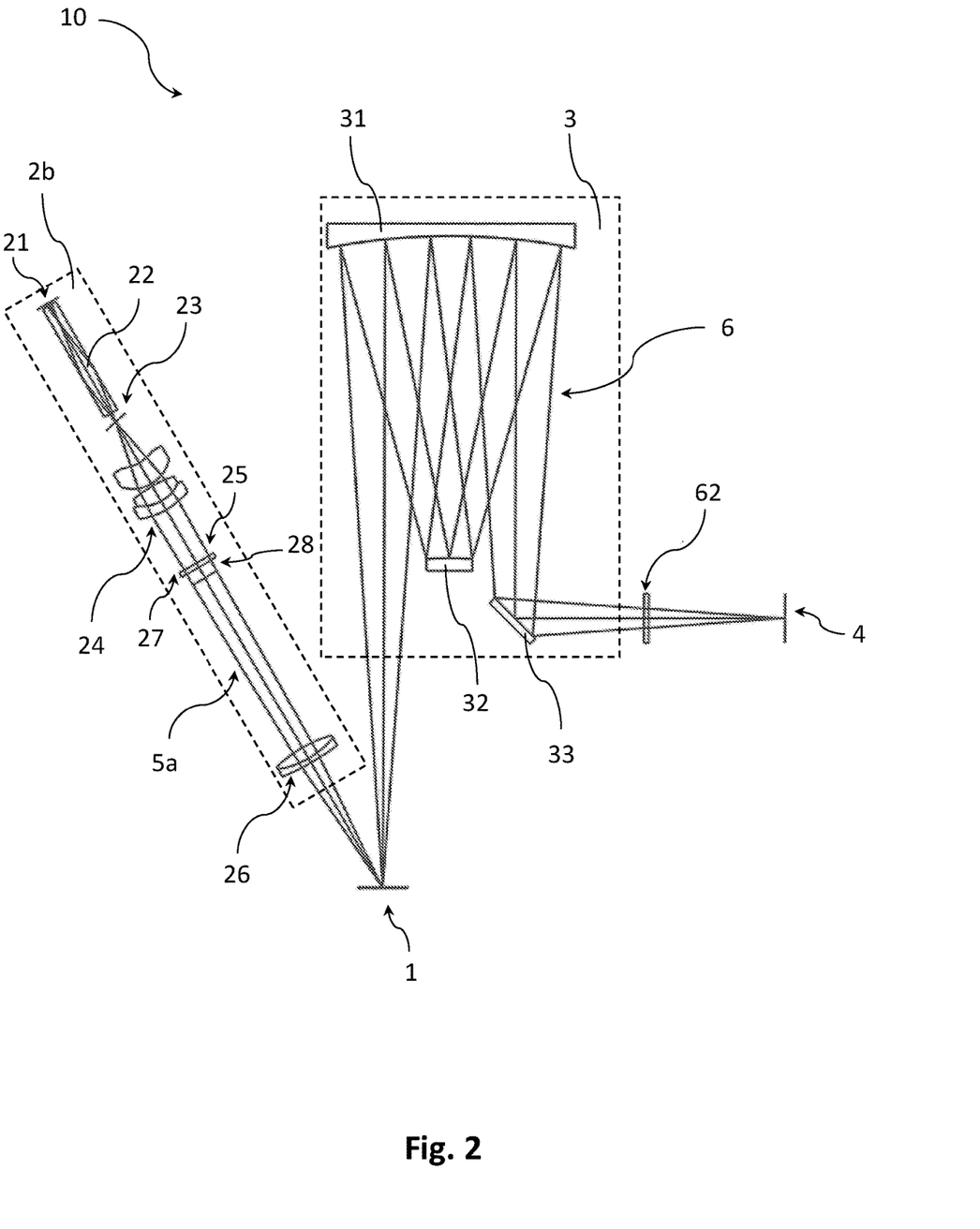
FIG. 2 illustrates an example optical measurement device using an epi-illumination unit and an Offner-type imaging system according to the present disclosure.

FIG. 2 illustrates an example optical measurement device using an epi-illumination unit 2b and an Offner-type imaging system 3. This setup is arranged to illuminate a sample carrier (e.g., a microwell plate) arranged in the sample holder 1 with illumination light 5. Fluorescent light emitted by the sample is imaged onto the detector 4 by the Offner-type imaging system 3.

The Offner-type imaging system 3 will be discussed first. As can be seen in FIG. 2, the imaging system includes a first curved mirror 31 and a second curved mirror 32. The mirrors 31, 32 (and the curved reflective elements according to the present disclosure in general) can be spherical elements. In other examples, the mirrors 31, 32 (and the curved reflective elements according to the present disclosure in general) can be aspherical elements.

In the example, of FIG. 2, the mirrors are 31, 32 arranged in an Offner-type arrangement. The imaging system is configured to image multiple measurement positions in the sample plane of the sample holder onto the detector. For instance, an array of measurement positions (e.g., an array of wells of a microwell plate or an array of other receptacles containing biological samples) can be imaged onto the detector at a time.

In the Offner-type arrangement of the imaging system 3, the center of curvature of the first and second curved mirrors 31, 32 are arranged at the same location. The imaging system has a magnification of substantially one (i.e., a magnification of 1+/−0.05). In other words, an image of a sample on an image plane of the detector 4 has substantially the same size as the actual sample (positioned in the object plane of the imaging system). In other examples, the imaging system 3 can be adapted so that the image of the sample on the image plane at the detector is larger than the actual sample by a factor of 2 or less (e.g., a factor of 1.2 or less). In still other examples the imaging system 3 is adapted so that the actual sample is larger than the image of the sample on the image plane of the detector by a factor of 2 or less (e.g., a factor of 1.2 or less). In other words, the imaging system can have a magnification between 1:2 and 2:1 (e.g., between 1.2:1 and 1:1.2) in other examples.

As can be seen in FIG. 2, the optical path of the imaging system is substantially symmetrical (apart from the folding by folding mirror 33 of the right "leg" of the optical path). This means that the optical path of a ray from a center of the sample to the first mirror 31 is equally long as the optical path of the same ray after it has left the first mirror 31 and propagates towards the detector 4. The same is true for the rays between the first mirror 31 and the second mirror 32.

In FIG. 2 the collection light is folded by a plane mirror 33 after having passed the first and second mirror 31, 32 of the Offner-type arrangement. In general, the optical path of the collection light in the imaging system of the present disclosure can be folded one or multiple times (e.g., by plane mirrors). The same is true for the optical path of the illumination light traversing the illumination system.

In FIG. 2 and in the remaining figures of the present disclosure the imaging device includes an Offner-type arrangement including two curved mirrors. However, the optical measurement devices of the present disclosure can also deploy different types of imaging devices including curved reflective elements providing a magnification between 1:2 and 2:1. In one example, the imaging system can include curved reflective elements configured in a different arrangement than an Offner-type arrangement. In addition or alternatively, the imaging system can include more than two curved reflective elements (e.g., curved mirrors) for imaging the sample plane onto the detector. For instance, the imaging system can include three or more, or four or more curved reflective elements. In still other examples, the optical imaging device can also include refractive elements that operate in transmission (e.g., one or more lenses).

The imaging device 3 (and particular the Offner-type arrangement) can exhibit comparatively low optical aberrations. This can be particularly advantageous when imaging small structures, e.g., microwell plates which can have wells with a diameter of 150 µm or lower and a spacing of 50 µm or lower as large aberrations might impair the system's capability to separate fluorescent light emanating from neighboring wells.

After the imaging system 3 for imaging the sample plane onto the detector 4 has been discussed in the previous sections, the illumination unit 2b will be explained in more detail subsequently.

The illumination unit includes a light source 21 for generating the illumination light 5a. In one example, the light source 21 includes one or more light emitting diodes (e.g., a plurality of light emitting diodes). For example, the light source 21 can include a plurality of light emitting diodes arranged in an array of light emitting diodes.

In other examples, the light source can include one or more gas discharge lamps or other discharge lamps. In still other examples, the light source can include one or more laser light sources (e.g., laser diodes). In general, the optical imaging devices of the present disclosure can be used with any suitable light source (depending on the characteristics of the light source, the optical elements in the optical path of the illumination unit can be modified depending on the nature of the light source). The light source 21 can be configured to emit light in wavelength band between 150 nm and 500 nm (e.g., between 300 nm and 430 nm).

After having been emitted from the light source 21, the illumination light 5a traverses a homogenizer 22. The homogenizer is adapted to increase a homogeneity of the illumination in the sample plane (i.e., a homogeneity of the illumination in the sample plane is higher with the homogenizer 22 compared to an equivalent illumination unit without the homogenizer 22).

This might be beneficial as the light source can emit light a fairly inhomogeneous pattern in some examples (e.g., in cases where the light source 21 includes multiple light emitting diode dies). This is particular relevant for critical lighting arrangements in which the light source is imaged onto the sample plane that can be used in some examples of the present disclosure (further explanations will follow below).

The illumination light can be guided in the homogenizer 22 by total internal reflection. Alternatively or in addition, the illumination light can be guided in the homogenizer 22 by reflection at a reflective coating or cover of the homogenizer 22 (e.g., a metal coating or a coating including one or more dielectric layers).

In the example of FIG. 2 the homogenizer includes a light guide in form of a rod in which the rays of the illumination light 5b propagate for a predetermined distance which leads to mixing and thus homogenization of the illumination light 5b. As a result, the illumination light at an output facet of the rod can be more homogenous than at the input facet.

The light guiding rods can comprise one of a tapered light guiding rod and a linear light guiding rod (as depicted in FIG. 2). The illumination light may propagate in the light guiding rod in a direction from a wider diameter to a smaller diameter of the light guiding rod. Alternatively, the illumination light may propagate from a smaller diameter to a wider diameter of the light guiding rod.

In other examples, the illumination units of the optical measurement devices of the present disclosure can include other homogenizers than a (mixing) rod. For instance, the illumination unit can include a scattering element (e.g., a scattering plate) adapted to homogenize the illumination light 5b.

In other examples, one of the light guiding rods adapted to guide and shape light discussed in European Patent Application No. EP 2713154 A1 can be employed in the illumination units according to the present disclosure, the disclosure of which is incorporated herein by reference.

The output of the rod 22 (or the output of any other homogenizer of the present disclosure) can be considered as secondary light source (the primary light source being the light source 21) of the illumination unit 2b. The output of the secondary light source can be imaged onto the sample plane by appropriate optical elements. In other words, the illumination unit uses a critical illumination arrangement in which the output of the homogenizer (i.e., the secondary light source) is imaged onto the sample plane of the optical measurement device. In this manner, a high brightness at the sample plane can be achieved in some examples. (See e.g., http://microscopy.berkeley.edu/courses/tlm/condenser/optics.html; and http://micro.magnet.fsu.edu/primer/anatomy/illumination.html, the disclosures of each of these references are incorporated herein by reference.)

In the example of FIG. 2, the optical elements form a relay lens 25, 26 configured to image the output of the homogenizer (i.e., the secondary light source) onto the sample plane. However, in other examples any other suitable optical element can be used (e.g., reflective optical elements). In addition, the example configuration of FIG. 2 including two sets of lenses (two of the lenses being achromatic lenses) is merely illustrative. In other examples, different numbers and/or configurations of lenses can be employed for imaging the output of the homogenizer 22 onto the sample plane.

Figure 3:
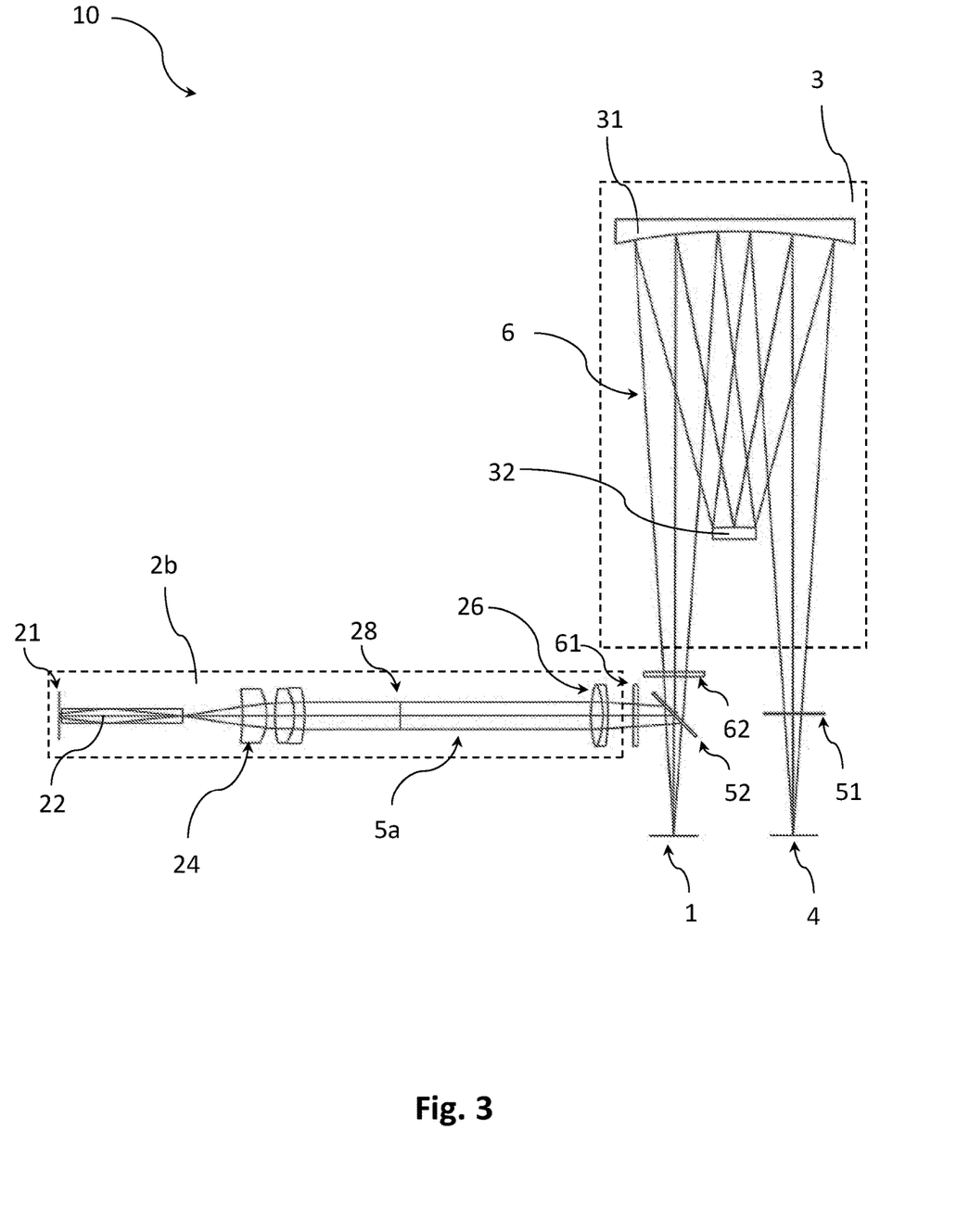
FIG. 3 illustrates another example optical measurement device using an epi-illumination unit and an Offner-type imaging system according to the present disclosure.
Figure 4:
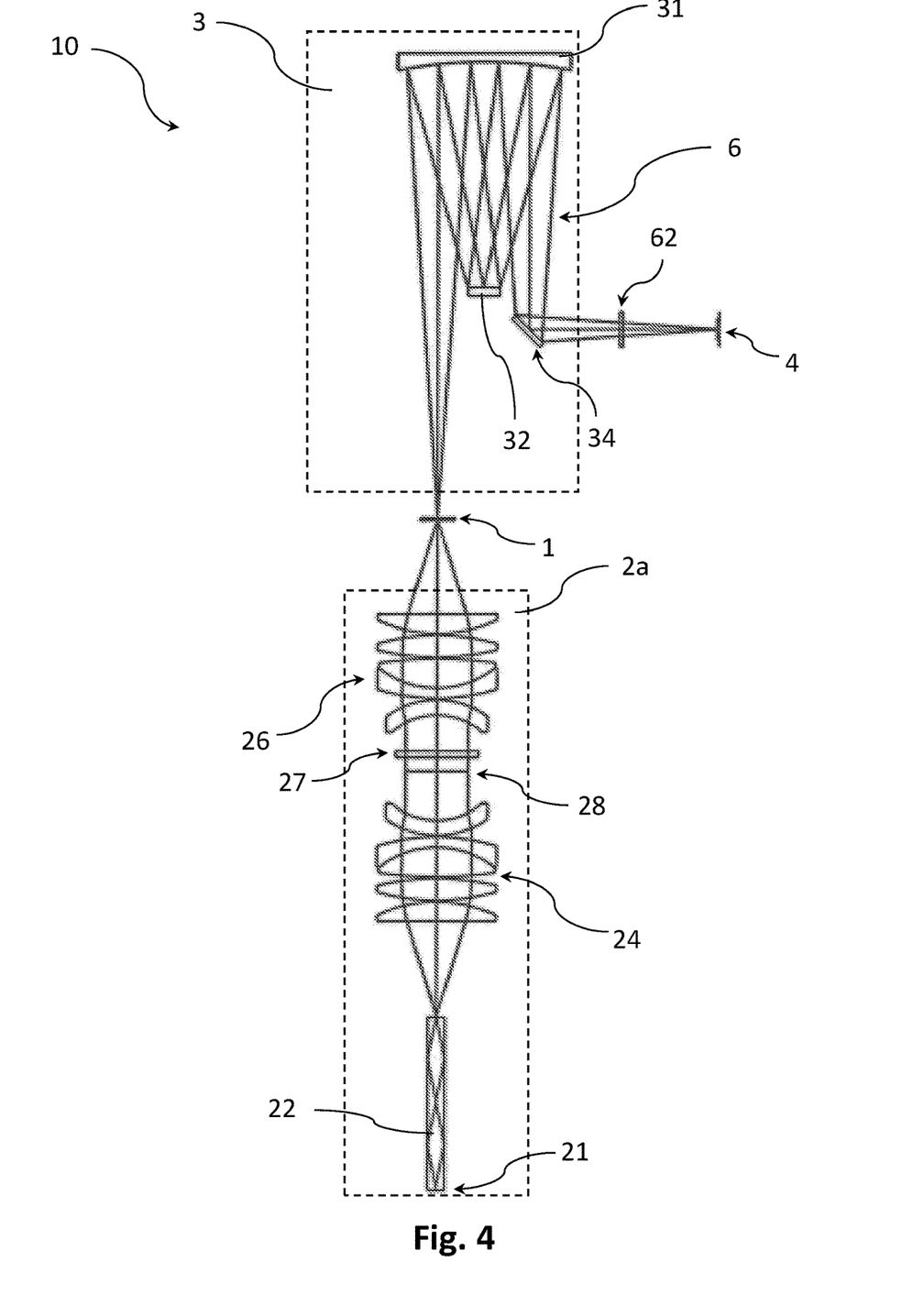
FIG. 4 illustrates an example optical measurement device using a trans-illumination unit and an Offner-type imaging system according to the present disclosure.

The examples of FIG. 2, FIG. 3 and FIG. 4 all depict illumination units using a critical lighting arrangement. However, in other examples the illumination units of the present disclosure can employ other lighting arrangements (e.g., using a Kohler arrangement in which an image of the light source is defocused in the sample plane and its conjugate image planes, see e.g., http://microscopy.berkeley.edu/courses/tlm/condenser/optics.html, the disclosure of which is incorporated herein by reference). In these examples (or also in other examples in which a homogenous illumination is of lesser importance), the illumination unit can also be designed without a homogenizer.

As already shortly discussed above, the illumination unit 2b is tilted relative to a normal direction of the sample plane (i.e., the main axis of the illumination light 5a and the normal on the sample plane form an angle larger than 5°, and smaller than 85°). This configuration can be used also for other illumination units discussed in the present disclosure. One advantage of a tilted configuration is that specular reflections of illumination light might not enter the imaging system and be imaged onto the detector 4 (which can lead to noise in the detection signal and/or require a more elaborate filter configured to block the illumination light).

In addition, the illumination unit 2b is arranged as epi-illumination unit, i.e., the illumination light impinges on the sample plane and the emitted light is collected at the same side of the sample plane. As will be discussed in connection with FIG. 4 below, the illumination units of the present disclosure can also be arranged in a trans-illumination configuration. In general, features of the illumination units described herein not specific to an epi-illumination unit can be also deployed in illumination units being arranged as trans-illumination unit (and vice versa).

As can be seen in FIG. 2, the illumination unit 2b and the imaging system 3 are completely separated. In other words, the illumination unit 2b and the imaging system 3 do not share an optical component. In this manner, the optical components can be adapted to the characteristics of the illumination light 5b and the collection light 6, respectively. This can be advantageous as adaptation of the optical components to both the illumination light 5b and the collection light 6 might be more complex (e.g., this might require using broadband antireflection coatings and/or optical elements corrected for multiple different wavelengths). In addition, having separate optical components in the illumination unit and the imaging device can allow to tailor the properties (e.g., a numerical aperture) of both systems independently.

The illumination unit 2b of FIG. 2 includes multiple optional elements which can be added or omitted depending on the circumstances and will be discussed subsequently.

On the one hand, the illumination unit 2b of FIG. 2 includes an additional titled field stop 23 arranged between the homogenizer 22 and the relay lens 25, 26. In this manner, a keystone aberration of the illumination light 5b at the sample plane can be reduced or even avoided. In other words, the illumination unit is arranged as a Scheimpflug-type illuminator. Without the tilted field stop 23, this type of aberration might occur due to the fact that the illumination unit 2b is tilted relative to the normal on the sample plane. Other compensation devices than a tilted field stop 23 for compensating keystone aberrations can also be utilized in other examples.

On the other hand, the illumination unit of FIG. 2 includes an aperture stop 27 (which might also be omitted in other examples). The aperture stop 27 is configured to determine a distribution of angles under which the rays of the illumination light 5b propagate towards a focus point (for example, an output numerical aperture of the illumination system 2b can be adjusted by the aperture stop 27). For instance, the aperture stop can include a pupil (if rays propagating under large angles shall be blanked out) or an annulus (if rays propagating under small angles shall be blanked out). Including an aperture stop 27 can be beneficial to avoid that rays of the illumination light 5b can enter the imaging system 3 and are imaged onto the detector 4 or reduce an amount of illumination light 5b entering the imaging system 3.

Furthermore, the illumination unit of FIG. 2 includes a circular beam stop 28. The circular beam stop 28 can be adapted and arranged to blank out illumination light rays propagating under small angles relative to an optical axis of the illumination light unit 2. In particular, the circular beam stop 28 can be adapted and arranged to blank out illumination light rays propagating under an angle of substantially zero (+/−2°). Such low-angle rays might be more likely to propagate through the imaging system and the wavelength-selective filter 62 and cause additional noise in the detector 4.

In addition, the illumination unit 2b includes a wavelength-selective filter 25 configured to shape a frequency spectrum of the illumination light 5b.

After having discussed the illumination unit 2b and the imaging system 3 in some detail, the remaining components of the optical measurement device of FIG. 2 will be treated next.

As already mentioned, the optical measurement device of FIG. 2 can be configured to detect fluorescence light (or other luminescence light) emitted from a sample in the sample carrier. The light source 21 of the illumination unit 2b can be adapted to match the absorption band of analytes to be sampled. As the fluorescence signal usually is spectrally shifted to longer wavelengths, the illumination light 5b and the collection light 6 can be spectrally separated. Therefore, the optical measurement device can include a wavelength-selective filter 62 adapted to reject illumination light propagating through the imaging system 3 (and let pass collection light 6). For example, the wavelength-selective filter 62 can include one or more dielectric layers arranged to reject illumination light propagating through the imaging system 3 (and let pass collection light 6).

After having discussed a first example of an optical measurement device according to the present disclosure in connection with FIG. 2, a second example of an optical measurement device according to the present disclosure will be discussed in connection with FIG. 3 in the subsequent sections.

As can be seen in FIG. 3, the illumination unit 2b and the imaging system 3 share several features with the respective components of the example of FIG. 2. Therefore, the features and variants of the respective components discussed in connection with FIG. 2 can also be employed in the optical measurement device of FIG. 3. The following discussion will focus on the differences.

On the one hand, the illumination unit 2b of FIG. 3 is arranged as epi-illumination unit but is not tilted. In other words, the illumination light 5b is focused onto the sample plane in a cone which is centered at the normal of the sample plane. This means that the rays of the illumination light 5b and the collection light 6 overlap at least partially along a portion of their respective paths.

In the example of FIG. 3, a dichroic mirror 52 is arranged to bring the illumination light 5b and the collection light 6 into overlap. The dichroic mirror 52 is configured to reflect (at least partially) the spectral components of the illumination light. At the same time, the dichroic mirror 52 is configured to transmit the spectral components of the collection light. In other examples a dichroic mirror can be arranged to transmit the illumination light and reflect the collection light (in this example, the positions of the illumination unit and the imaging system can be flipped compared to the positions in FIG. 3).

In the example of FIG. 3 an output numerical aperture of the illumination unit 2b is equal to an input numerical aperture of the imaging system 3. In other examples, this situation can be different. For instance, the output numerical aperture of the illumination unit 2b could be larger than the input numerical aperture of the imaging system (similar as in the trans-illumination configuration shown in FIG. 4). In this manner, a larger quantity of illumination photons can be delivered to the sample located in the sample plane.

In addition or alternatively, the illumination unit of FIG. 3 can include an aperture stop (e.g., an annular aperture stop). The aperture stop can be designed and arranged to blank rays propagating under angles that can be received by the imaging system 3. For example, the illumination unit can provide an annular illumination pattern (e.g., by employing an annular aperture stop).

The optical measurement device of FIG. 3 can optionally include a compensation element 51 arranged in the collection light path. In one example, the compensation element 51 includes a plate having the same optical thickness as the dichroic mirror 52. In addition, the compensation element 51 can be tilted about an axis which is orthogonal to a tilt axis of the dichroic mirror 52 (the tilt of the compensation element cannot be seen in FIG. 3 as FIG. 3 shows a cross-sectional view of the device). As can be seen in FIG. 3, the compensation element 51 can be included at a position in the optical path of the imaging system 3 which corresponds to the position of the dichroic mirror 52 mirrored at a center axis of the imaging system 3. In other words, a beam waist and opening angle of the collection light at the dichroic mirror 52 and the compensation element 51 are (substantially) equal. The compensation element 51 can correct (at least partially) astigmatic errors introduced by the dichroic mirror. The dichroic mirror 52 might introduce an astigmatic error as the two transversal polarizations in the collection light 6 traverse different optical paths in the dichroic mirror 52. The "flipped" compensation element 51 can (substantially) reverse this effect.

The detector 4 will be discussed subsequently. The following explanations regarding the detector 4 are not specific to the optical measurement device of FIG. 3.

As the imaging systems of the present disclosure are configured to image multiple detection positions in the sample plane (e.g., multiple wells of a microwell plate or other receptacles configured to contain a biological sample) at a time, the detectors are configured to spatially resolve the image produced by the imaging system. In one example, the detector 4 is configured to cover each measurement position with multiple pixels (e.g., with more than 5 pixels, with more than 10 pixels or with more than 50 pixels). In devices where a magnification of the imaging system is 1 (or close to one), this means that the sensor size of pixels of the imaging device is smaller than an area of each measurement position (e.g., a surface area of a well of a microwell plate or a surface area of another receptacle configured to contain a biological sample). In one example, a size of a pixel of the detector 4 is smaller than 20 µm (e.g., smaller than 10 µm). A surface area of a well of a microwell plate can be lower than 0.25 $mm^2$ (e.g., the surface area can range between 400 $µm^2$ and 0.04 $mm^2$) in some examples.

The detector 4 can include any suitable light detection device. In one example, the detector 4 includes one or more CCD (charge coupled device) or CMOS sensors including a plurality of pixels. In other examples, the detector 4 can include a multichannel plate or another spatially resolved photomultiplier. In still other examples, the detector can include an array of photodiodes (e.g., an array of PIN diodes or APDs [avalanche photo diodes]) or other light-transducing elements.

Moreover, as can be seen in FIG. 3, the optical path of the imaging system is not folded by additional folding elements. As a consequence, the image plane 1 and the detector 4 are arranged at the same height in a symmetrical manner compared to a center plane of the imaging system 3. As already discussed above, folding elements can be added to adapt the size of the imaging system 3 to different circumstances and analyzer environments.

Last, the optical measurement device of FIG. 3 includes another wavelength-selective filter 61 on the illumination side. This wavelength-selective filter 61 can be adapted to shape (e.g., to narrow) an excitation spectrum of the illumination light 5a. In one example, the wavelength-selective filter 61 can be adapted to narrow the spectrum of the illumination light to a spectrum adapted for excitation of particular fluorescent molecules (and blank out wavelengths which do not efficiently excite the particular fluorescent molecules). In addition, the wavelength-selective filter 61 can be configured to block the wavelengths that are transmitted by the wavelength-selective filter 62 adapted to reject illumination light. This can further improve the signal-to-noise ratio of the optical measurement device in some examples.

In connection with FIG. 2 and FIG. 3, two example optical measurement devices using epi-illumination arrangements have been discussed. FIG. 4 shows an optical measurement device in which the illumination unit 2a is arranged as a trans-illumination unit. This configuration will be discussed subsequently.

As can be seen in FIG. 4, the imaging system 3 is arranged in a similar manner as the imaging system of the device of FIG. 2. All refinements and variants discussed for the imaging systems of FIG. 2 and also FIG. 3 can also be employed in the device of FIG. 4.

Moreover, the illumination unit 2a of FIG. 4 can also include a light source 21 and a homogenizer 22 as discussed above.

A first difference between the device of FIG. 4 and the previously discussed devices is the trans-illumination arrangement of the illumination unit 2a. In other words, the illumination light 5a impinges on the sample from one side and the fluorescent light is collected at the other side of the sample plane.

As can be seen in FIG. 4, an output side numerical aperture of the illumination unit 2a is larger than an input side numerical aperture of the imaging system 3. In one example, an output side numerical aperture of the illumination unit 2a can be 0.5 or smaller (e.g., smaller than 0.4). The input side numerical aperture of the imaging system can be 0.1 or smaller (e.g., between 0.06 and 0.08).

In general, as discussed above, this could also be achieved in the devices of FIG. 2 and FIG. 3. However, the trans-illumination arrangement of the device of FIG. 4 simplifies the setup of large output side numerical aperture illumination. An epi-illumination arrangement might not allow (very) large numerical aperture illumination (or this would at least be fairly difficult to realize) as this would require adding optical components having large pupils comparatively close to the sample plane. These components could interfere with the collection light or impair an optical quality of the imaging system (if both the illumination light and the collection light traverse these components). In contrast to that, the trans-illumination arrangement of the illumination unit 2a of FIG. 4 allows for using optical components with large pupils without interfering with the collection light 6.

Having a large output side aperture of the illumination unit can be advantageous as a larger quantity of illumination light reaches the sample. In systems detecting fluorescence light (or other luminescent light signals) this can be advantageous even if an input numerical aperture of the imaging system might be (considerably) smaller than the output side aperture of the illumination system (which might be the case when using the relatively low-magnification imaging systems of the present disclosure). After all, a direction of the re-emitted photons is (substantially) independent from the direction of absorbed photons in many fluorescent samples. Therefore, the rays of illumination light impinging onto the sample under large angles increase a signal strength of emitted photons in all spatial directions.

In the example of FIG. 4, the illumination unit can include an annular aperture stop that is configured to block rays propagating under small angles compared to the main optical axis of the illumination unit 2a. In other words, the annular aperture stop produces an annular illumination pattern at the sample plane. In addition, the annular aperture stop can be configured to avoid that rays of the illumination ray enter and are imaged onto the detector 4 by the imaging system. For instance, an inner output numerical aperture of the ring shaped output of the illumination system 2a can be larger than the input side numerical aperture of the imaging system 2.

As can be seen in FIG. 4, the illumination unit 2a can also include a relay lens 24, 26. Compared to the relay lens 25, 26 of FIG. 2, the relay lens 24, 26 of FIG. 4 is more complex. However, in both cases the relay lens merely serves to image the output of the homogenizer 22 (second light source) onto the sample plane to achieve a critical lighting condition. Therefore, any assembly of refractive elements forming a relay lens (e.g., two plano-convex lenses) can be used in general. However, in order to produce an image of the output of the second light source with low aberration on the sample plane, an assembly including multiple lens elements (as shown in FIG. 2, FIG. 3 and FIG. 4) might be used. This is also the reason why the relay lens 24, 26 of FIG. 4 is more complex: As the high output numerical aperture of the illumination unit 2a involves handling beams propagating under larger angles/being more off-central than the beams of the illumination units of FIG. 2 and FIG. 3, aberrations that might still be tolerable in the devices of FIG. 2 and FIG. 3 might become an issue in the device of FIG. 4. Thus, a more elaborate correction of aberrations might be required or desired.

After different aspects and features of an example optical measurement device have been discussed in the previous sections in connection with FIG. 1 to FIG. 4, aspects of the integration of the optical measurement devices of the present disclosure in an analyzer for biological samples will be discussed next in connection with FIG. 5.

Figure 5:
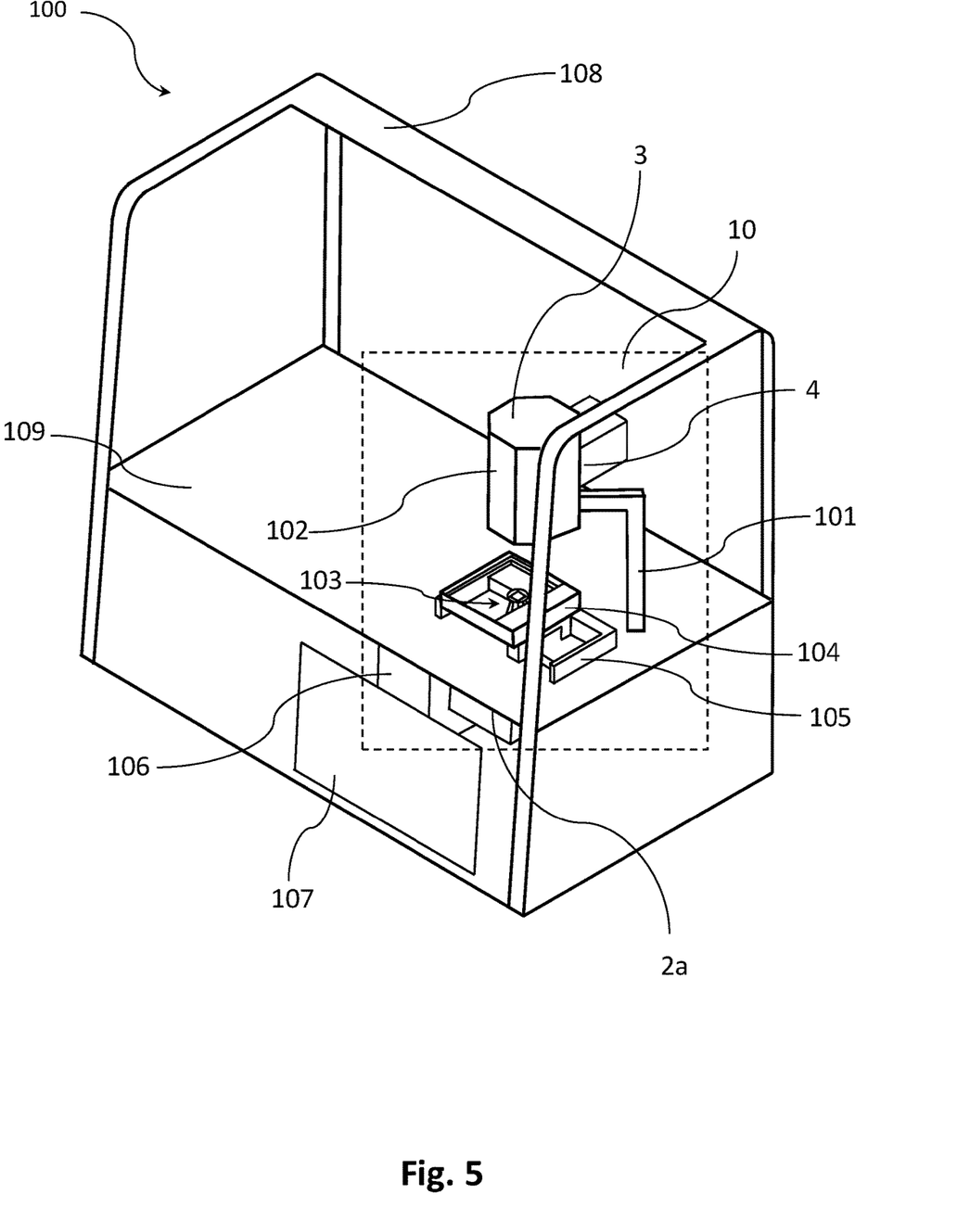
FIG. 5 illustrates an example analyzer according to the present disclosure.

FIG. 5 shows an example analyzer 100 for biological samples. In one example, the analyzer for biological samples 100 can include one or more thermal cyclers configured to amplify segments of DNA or other nucleotides via the polymerase chain reaction (PCR). Each thermal cycler can have a thermal block with receptacles where tubes, microwell plates or other biological sample holders holding the reaction mixtures including the biological samples can be inserted. The thermal cycler can be configured to raise and lower the temperature of the block according to a pre-programmed or dynamically adapted profile.

In the example of FIG. 5 the one or more thermal cyclers (not shown in FIG. 5 for the sake of illustration) are arranged on the left hand side of a housing 108 of the analyzer 100. The optical measurement device 10 is arranged on the right hand side of the housing 108. In the example of FIG. 5, the optical measurement device 10 is configured as a trans-illumination device.

The analyzer 100 can include transfer devices (not shown in FIG. 5) to transfer sample carriers (e.g., microwell plates) from the one or more thermal cyclers into a sample holder of the optical measurement device 10 (which will be discussed in more detail below). In addition, the analyzer 100 can include one or more ports through which sample carriers can be inserted into the analyzer (not shown in FIG. 5).

The illumination unit 2a is at least partially arranged below a central horizontal plane 109 of the analyzer. As can be seen in FIG. 5, the illumination unit 2a includes a volcano-shaped output side element 103 over which a sample to be analyzed can be positioned (in other examples the configuration of the output side of the illumination unit can be constructed differently).

The volcano-shaped output side element 103 encloses the last part of the optical path of the illumination light (as shown, e.g., in FIG. 4). Moreover, the output side element 103 defines an aperture through which the illumination light can exit and illuminate a sample. A sample plane of the optical measurement device 10 is located above the aperture of the output side element 103.

The optical components of the illumination unit 2a (e.g., including a relay lens, a homogenizer, an aperture stop and a light source) are arranged below the central horizontal plane 109. In the example of FIG. 5, the components of the illumination unit 2a are arranged in a common housing.

The components of the illumination unit 2a can be arranged in a modular manner. For instance, the homogenizer, the light source and/or the relay lens can be configured as separate modules (which can be configured to be removed and inserted separately). In one example, the illumination unit 2a can include a port to which a light source can be removably attached (e.g., by means of a C mount or other suitable mount).

The analyzer 100 further includes a sample holder 104 coupled to an actuator 105. The sample holder 104 is configured to receive one or more sample carriers (e.g., a microwell plate) and to position the one or more sample carriers in the sample plane of the optical measurement device 10.

The actuator 105 is configured to move the sample holder 104 in one or two orthogonal spatial directions. In this manner, different portions of the one or more sample carriers which are supported by the sample holder can be moved into the field of view of the optical measurement device 10. In this manner, sample carriers having a surface area larger than the field of view of the optical measurement device 10 (or more than one sample carriers arranged in the sample holder) can be sequentially scanned.

Furthermore, the optical measurement device 10 of FIG. 5 includes an optical imaging system 3 including two or more curved reflective elements adapted to image the sample plane onto the detector with a magnification of between 2:1 and 1:2 (e.g., one of the imaging systems discussed in connection with FIG. 1 to FIG. 4) arranged in a housing 102. The optical measurement device 10 further includes a detector 4.

In the example of FIG. 5, the optical imaging system 3 and the detector 4 are arranged above the central horizontal plane 109 of the analyzer 100. For example, the housing 102 of the imaging system can be supported by one or more support structures 101 mounted on the central horizontal plane 109.

The analyzer further includes a control unit 106 which can be configured to control the operations of the optical measurement device 10. For example, the control unit 106 can be configured to automatically perform measurements on biological samples. In addition, the control unit can be configured to control the operations of further components of the analyzer. For instance, the control unit 106 can be configured to control the operation of the actuator 105 and/or a transfer device (not shown in FIG. 5). In addition, the control unit 106 can be configured to the operations of the one or more thermal cyclers of the analyzer 100.

In the example of FIG. 5, the analyzer 100 of FIG. 5 further includes an optional display 107 adapted to display information regarding the operation of the optical measurement device 10 (and optionally other elements of the analyzer 100). In one example, the display can be a touch display through which a user can input control information for the optical measurement device 10 (and/or other components of the analyzer 100).

In connection with FIG. 5 a particular layout of the optical measurement device 10 has been discussed. However, in other examples the optical measurement device 10 can be integrated in an analyzer 100 in different other ways. In general, any of the optical measurement devices 10 discussed in connection with FIG. 1 to FIG. 4 above can be integrated in an analyzer 100.

For example, the optical measurement device 10 can be an optical measurement device including an epi-illumination unit (e.g., as discussed in connection with FIG. 2 or FIG. 3).

In addition or alternatively, the optical measurement device 10 can be arranged differently in an analyzer 100. For instance, the illumination unit and the imaging system can be located at different positions. In addition, the illumination and/or detection light path can be folded one or several times. In this manner, the optical measurement device 10 can be adapted to the spatial requirements of a respective analyzer.

In some examples, an analyzer can also be equipped with two or more optical measurement devices according to the present disclosure.

In the example of FIG. 5, the analyzer includes an actuator 105 configured to move a sample carrier positioned in a sample holder in two orthogonal directions (which might be lateral directions labelled as "x-direction" and "y-direction"). However, in other examples the optical measurement device 10 can include a sample holder which is stationary relative to the illumination unit and the imaging system. In this case, the sample carrier can be completely imaged in a "single-shot." In still other examples, the actuator can be configured to move a sample carrier in three orthogonal spatial directions (e.g., in an analyzer which is configured to scan in two lateral directions but also in an axial direction for imaging different planes of a sample carrier). In still other examples, the optical measurement device can be configured to move relative to the sample carrier (which can be stationary in this case) in one, two or three orthogonal spatial direction.

An analyzer for analyzing DNA or other nucleotides amplified via the polymerase chain reaction (PCR) including one or more thermal cyclers has been discussed in connection with FIG. 5. However, as already discussed above, the analyzer 100 can additionally be configured to determine via various chemical, biological, physical, optical or other technical procedures a parameter value of a biological sample or a component thereof.

In the previous passages different optical measurement devices have been described. However, the present disclosure also relates to imaging methods. In one aspect, a method for imaging a sample carrier having an array of measurement positions containing samples comprises illuminating the array of measurement positions, collecting light emitted from all measurement positions of the array of measurement positions at a time and imaging the collected light onto a detector by using two or more curved reflective elements adapted to image the sample plane onto the detector with a magnification of between 2:1 and 1:2.

In addition, the method for imaging a sample can include any one of the steps of the techniques described above in connection with the optical measurement devices of the present disclosure.

The imaging methods of the present disclosure can be embodied in instructions on a computer-readable medium which when executed by a computer or computing system can cause the computer or computing system to carry out the steps of the methods for calibration and/or error detection of the present disclosure.

Furthermore, the particular features, structures, or characteristics may be combined in any suitable combinations and/or sub-combinations in one or more embodiments or examples.

In the preceding detailed description multiple examples of optical measurement devices and methods of the present disclosure have been discussed. However, the optical measurement devices and methods of the present disclosure can also be configured as described herein, throughout the specification and claims.

All patents, patent applications, publications, and descriptions mentioned herein are incorporated by reference in their entirety for all purposes. None is admitted to be prior art.

The invention claimed is:

1. An optical measurement device, comprising:
   a sample holder defining a sample plane, the sample holder comprising a sample carrier including an array of measurement positions in the sample plane;
   an illumination unit comprising an output numerical aperture and a light source to generate and project illumination light onto the sample plane;
   a light detecting device; and
   an optical imaging system operably connected to the light detecting device and positioned substantially parallel to the sample plane, the optical imaging system comprising a numerical aperture and two or more curved reflective elements to image light emitted from the sample plane onto the light detecting device with a magnification of between 2:1 and 1:2,
   wherein the optical imaging system images light emitted from all measurement positions of the array substantially simultaneously onto the light detecting device, and the output numerical aperture is greater than the numerical aperture.

2. The optical measurement device of claim 1, wherein the two or more curved reflective elements include two or more curved mirror elements.

3. The optical measurement device of claim 2, wherein the two or more reflective elements are arranged in an Offner-type configuration.

4. The optical measurement device of claim 1, wherein the magnification of the optical imaging system is between 1.2:1 and 1:1.2.

5. The optical measurement device of claim 1, wherein the magnification of the optical imaging system is substantially 1.

6. The optical measurement device of claim 1, wherein the illumination unit is an epi-illumination unit.

7. The optical measurement device of claim 1, wherein the illumination unit further comprises a homogenizer to increase the homogeneity of light projected onto the sample plane.

8. The optical measurement device of claim 1, wherein the illumination unit is a Scheimpflug-type illuminator.

9. The optical measurement device of claim 1, wherein the illumination unit is a trans-illumination unit.

10. The optical measurement device of claim 1, wherein the sample carrier is a microwell plate.

11. The optical measurement device of claim 1, wherein the light detecting device includes a plurality of pixels having a pixel size which is smaller than an area of a measurement position in the array.

12. The optical measurement device of claim 1, wherein the optical measurement device further comprises (i) a dichroic mirror positioned in an optical path between the sample plane and the optical imaging system, and (ii) a correction element comprising a plate having the same optical thickness as the dichroic mirror, wherein the plate is tilted about an axis orthogonal to a tilt axis of the dichroic mirror to thereby at least partially correct light aberrations induced by the dichroic mirror.

13. A polymerase chain reaction (PCR) system comprising the optical measurement device of claim 1.

14. A method of using an optical measurement device of claim 1 to image light emitted from a sample carrier having an array of measurement positions containing samples, the method comprising:
   (a) illuminating the array of measurement positions;
   (b) collecting light emitted from all measurement positions of the array of measurement positions substantially simultaneously; and
   (c) imaging light collected in the step (b) onto a light detecting device using two or more curved reflective elements to image light emitted from the sample plane onto the light detecting device with a magnification of between 2:1 and 1:2.

* * * * *